(12) United States Patent
Murray (10) Patent No.: US 9,590,122 B2
(45) Date of Patent: Mar. 7, 2017

(54) FISH EYE LENS ANALYZER (71) Applicant: Siemens Healthcare Diagnostics Inc., Tarrytown, NY (US)

(72) Inventor: Paul Murray, Sudbury (GB)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/401,568

(22) PCT Filed: May 17, 2013

(86) PCT No.: PCT/US2013/041510
§ 371 (c)(1),
(2) Date: Nov. 17, 2014

(87) PCT Pub. No.: WO2013/173674
PCT Pub. Date: Nov. 21, 2013

(65) Prior Publication Data
US 2015/0171236 A1    Jun. 18, 2015

Related U.S. Application Data

(60) Provisional application No. 61/648,839, filed on May 18, 2012.

(51) Int. Cl.
*H01L 31/02* (2006.01)
*H01L 31/0232* (2014.01)
*G01N 21/84* (2006.01)

(52) U.S. Cl.
CPC ... *H01L 31/02325* (2013.01); *G01N 21/8483* (2013.01)

(58) Field of Classification Search
CPC .................. H01L 31/02325; G01N 21/8483
See application file for complete search history.

(56) References Cited

U.S. PATENT DOCUMENTS

| 4,755,058 A | 7/1988 | Shaffer |
| 5,241,369 A | 8/1993 | McNeil et al. |
| 5,313,542 A * | 5/1994 | Castonguay ......... G01N 21/474 250/227.28 |

(Continued)

FOREIGN PATENT DOCUMENTS

| CN | 102272580 A | 12/2011 |
| EP | 0165535 A2 | 12/1985 |

(Continued)

OTHER PUBLICATIONS

International Search Report and Written Opinion of International Application No. PCT/US2013/041510 dated Oct. 10, 2013.

(Continued)

*Primary Examiner* — Tony Ko
(74) *Attorney, Agent, or Firm* — Kyle D. Petaja (57) ABSTRACT

An imaging device is disclosed. The imaging device has a housing, a detector positioned within the housing and has a field of view encompassing one or more target area within the housing to be imaged, a wide-angle lens operatively coupled to the detector, and a support positioned at the target area and configured to receive one or more test component. The wide-angle lens is operatively coupled to the detector such that the detector receives image data of the target area through the wide-angle lens.

15 Claims, 7 Drawing Sheets

(56) References Cited

U.S. PATENT DOCUMENTS

| | | | |
|---|---|---|---|
| 5,408,535 A | 4/1995 | Howard, III et al. | |
| 5,449,898 A | 9/1995 | Dosmann | |
| 5,477,326 A | 12/1995 | Dosmann | |
| 5,518,689 A | 5/1996 | Dosmann et al. | |
| 5,654,803 A | 8/1997 | Howard, III et al. | |
| 5,661,563 A | 8/1997 | Howard et al. | |
| 5,877,863 A | 3/1999 | Ross et al. | |
| 6,180,409 B1 | 1/2001 | Howard, III et al. | |
| 8,482,723 B2 * | 7/2013 | Tsukii | G01N 15/1434 356/73 |
| 8,547,557 B2 * | 10/2013 | Jansen | G01B 9/04 356/495 |
| 2005/0019942 A1 | 1/2005 | Sloane et al. | |
| 2006/0257284 A1 | 11/2006 | Rheinheimer et al. | |
| 2007/0064220 A1 | 3/2007 | Stock et al. | |
| 2008/0097225 A1 | 4/2008 | Tearney et al. | |
| 2009/0116023 A1 | 5/2009 | Wadman | |
| 2010/0016673 A1 | 1/2010 | Bandy et al. | |
| 2011/0122418 A1 | 5/2011 | Jansen | |
| 2011/0279805 A1 | 11/2011 | Ryzhikov et al. | |

FOREIGN PATENT DOCUMENTS

| | | |
|---|---|---|
| EP | 0762111 A1 | 3/1997 |
| JP | 3628727 B2 | 3/2005 |
| WO | 9412864 A1 | 6/1994 |
| WO | 2009048833 A1 | 4/2009 |
| WO | 2011027315 A1 | 3/2011 |
| WO | 2012012499 A1 | 1/2012 |

OTHER PUBLICATIONS

European Supplementary Search Report and Search Opinion of European Application No. EP 13791055 dated Dec. 16, 2015.

\* cited by examiner

FISH EYE LENS ANALYZER

The entirety of U.S. Provisional Application Ser. No. 61/648,839, filed on May 18, 2012, is hereby expressly incorporated herein by reference.

FIELD OF THE INVENTION

The present invention relates to a readhead for a photometric diagnostic instrument, such as a reflectance spectroscope, for performing tests on a sample of fluid to be analyzed.

BACKGROUND OF THE INVENTION

Reagent test strips are widely used in the field of clinical chemistry. A test strip usually has one or more test areas, and each test area is capable of undergoing a color change in response to contact with a liquid specimen. The liquid specimen usually contains one or more constituents or properties of interest. The presence and concentrations of these constituents of interest in the specimen are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. For this reason, a reflectance spectroscope is commonly used to analyze samples of body fluid. A conventional spectrophotometer determines the color of a urine sample disposed on a white, non-reactive pad by illuminating the pad and taking a number of reflectance readings from the pad, each having a magnitude relating to a different wavelength of visible light. Today, strip reading instruments employ a variety of area array detection readheads utilizing CCD (charge-coupled device), CID (charge-injection device) or PMOS detection structures for detecting color changes to the test strips. The color of the urine on the pad may then be determined based upon the relative magnitudes of red, green and blue reflectance signals.

Conventional spectrophotometers may be used to perform a number of different urinalysis tests utilizing a reagent strip on which a number of different reagent pads are disposed. Each reagent pad is provided with a different reagent which causes a color change in response to the presence of a certain type of constituent in urine such as leukocytes (white blood cells) or red blood cells. Typical analytes of interest for urine include glucose, blood, bilirubin, urobilinogen, nitrite, protein, and ketone bodies. After adding color-developing reagents to urine, the foregoing analytes of interest have the following colors: glucose is bluish green; bilirubin, urobilinogen, nitrite, and ketone bodies are green; and blood and protein are red. The color developed in a particular analyte defines the characteristic discrete spectrum for absorption of light for that particular analyte. For example, the characteristic absorption spectrum for color-developed glucose falls within the upper end of the blue spectrum and the lower end of the green spectrum. Reagent strips may have ten different types of reagent pads.

For example, to detect on immunotest strips or chemistry test strips the presence of blood in a person's urine, conventional reflectance spectroscopes have been used to detect the presence of blood in a urine sample disposed on a reagent pad. Any blood present in the urine reacts with the reagent on the reagent pad, causing the reagent pad to change color to an extent which depends on the concentration of the blood. For example, in the presence of a relatively large concentration of blood, such a reagent pad may change in color from yellow to dark green.

A conventional reflectance spectroscope detects the concentration of the blood by illuminating the reagent pad and detecting, via a conventional reflectance detector, the amount of light received from the reagent pad, which is related to the color of the reagent pad. Based upon the magnitude of the reflectance signal generated by the reflectance detector, the spectroscope assigns the urine sample to one of a number of categories, e.g. a first category corresponding to no blood, a second category corresponding to a small blood concentration, a third category corresponding to a medium blood concentration, and a fourth category corresponding to a large blood concentration.

In one type of reflectance spectroscope an optical system in the form of a readhead is used in which a light bulb is disposed directly above the reagent pad to be tested and a reflectance detector is disposed at a 45 degree angle to the horizontal surface of the reagent pad. Light passes through a first vertical optical path from the illumination source to the reagent pad and through a second optical path, disposed 45 degrees with respect to the first optical path, from the reagent pad to the reflectance detector.

Other devices have been designed to illuminate a reagent pad. For example, U.S. Pat. No. 4,755,058 to Shaffer discloses a device for illuminating a surface and detecting the intensity of light emitted from the surface. The surface is directly illuminated by a plurality of light-emitting diodes disposed at an acute angle relative to the surface. U.S. Pat. No. 5,518,689 to Dosmann, et al. discloses a diffused light reflectance readhead in which one or more light-emitting diodes are used to illuminate a reagent pad and in which light from the reagent pad is detected by a light sensor.

Many reflectometer machines are small enough and inexpensive enough to be usable in physician offices and smaller laboratories, for example, and therefore are able to provide individual doctors, nurses and other caregivers with powerful medical diagnostic tools. For example, U.S. Pat. No. 5,654,803, which is assigned to the assignee of the present disclosure and is incorporated herein by reference in its entirety, discloses an optical inspection machine for determining non-hemolyzed levels of occult blood in urine using reflectance spectroscopy. The machine is provided with a light source for successively illuminating a plurality of different portions of a reagent pad on which a urine sample is disposed, and a detector array for detecting light received from the reagent pad and generating a plurality of reflectance signals in response to light received from a corresponding one of the different portions of the reagent pad. The machine is also provided with means for determining whether the magnitude of one of the reflectance signals is substantially different than the magnitude of another of the reflectance signals. Where the body-fluid sample is urine, this capability allows the machine to detect the presence of non-hemolyzed levels of occult blood in the urine sample.

U.S. Pat. No. 5,877,863, which is also assigned to the assignee of the present disclosure and is incorporated herein by reference in its entirety, shows an optical inspection machine for inspecting a liquid sample, such as urine, using reflectance spectroscopy. The machine includes a readhead for illuminating a target area substantially uniformly via only a single light-emitting diode and receiving light from the target area so that reagent tests may be performed. The readhead is provided with a housing, first and second light sources mounted in a fixed position relative to the housing, a light guide mounted to receive light from each of the light sources which conveys, when only one of the light sources is illuminated, substantially all of the light from the light source to illuminate a target area substantially uniformly, and a light detector coupled to receive light from the target area. Each of the first and second light sources is composed of only a single light-emitting diode for emitting substantially monochromatic light of a different wavelength.

Other optical readers are known that do not use reflectance, but rather capture an image of the test strips and convert the captured signal to RGB or to another format from which the color of the reagent pads on the test strip can be determined. U.S. Pat. No. 5,408,535, which is also assigned to the assignee of the present disclosure and is incorporated herein by reference in its entirety. These optical readers can also be used to read slides or other diagnostic tests.

As mentioned above, such optical inspection machines provide individual doctors, nurses and other caregivers with powerful medical diagnostic tools. Since space is limited, there is a need to make these devices even smaller. According to one aspect of the present disclosure, this can be accomplished by reducing the optical path between the detector and the reagent pad. Furthermore, a need exists to permit the device to read more than one reagent strip at a time or a combination of urine strips and reagent cartridges at the same time. The spectrometers of the prior art have not met these needs.

SUMMARY OF THE DISCLOSURE

Briefly, in accordance with the present disclosure, these and other objects are attained by providing a readhead including a fish eye lens operatively coupled to a detector.

The disclosure in one aspect describes a new and improved reflectance spectroscope including a fish eye lens operatively coupled to a detector. The detector can then be positioned directly above the target to be imaged and/or much closer to the target to be imaged or may be positioned so that multiple targets lying adjacent to each other may be imaged simultaneously.

The disclosure in another aspect is a new and improved method for imaging one or more reagent strips or cartridges including the steps of providing a fish eye lens operatively coupled to a detector. The detector is then positioned much closer to the reagent strip or cartridge to be imaged or may be positioned so that multiple reagent strips or cartridges or slides may be imaged simultaneously. The reagent strips, cartridges, or slides are then imaged. One aspect of the invention further includes software for converting the raw data image taken by the fish eye lens coupled detector and converting the raw data image into data representing a test result or metadata necessary to determine a test result.

The disclosure in a further aspect describes a kit including a fish eye lens operatively coupled to a detector. In another aspect, the disclosure describes a kit including a fish eye lens structured and arranged to be operatively coupled to a detector. The kit may include coupling instructions. The kit may also include instructions on positioning the detector to image one or more reagent strips or cartridges.

Additional features and advantages of the disclosure will be made apparent from the following detailed description of illustrative embodiments that proceeds with reference to the accompanying drawings.

BRIEF DESCRIPTION OF THE DRAWINGS

A more complete appreciation of the present disclosure and many of the attendant advantages thereof will be readily understood by reference to the following detailed description when taken in conjunction with the accompanying drawings, in which.

DESCRIPTION OF THE PREFERRED EMBODIMENTS

Throughout this document, the terms "couple" and "coupled" refer to elements which can be directly connected together or one or more intervening elements may also be present. In contrast, the terms "directly couple" and "directly coupled" refer to elements that are directly connected with no intervening elements present.

In one aspect, the disclosure describes an assembly including an imager, a detector capable of capturing image data, and a wide angle lens, often called a fish eye lens. The fisheye lens can be a wide-angle lens that takes in an extremely wide, hemispherical image. For example, the fisheye lens can be a miniature fisheye lens designed for small-format CCD/CMOS imagers. Format sizes may include ¼" (active area 3.6 mm×2.7 mm), ⅓" (active area 4.8 mm×3.6 mm) and ½" (active area 6.6 mm×4.8 mm). The imager can be a camera or other image capture device. Preferably, the imager is a 2D CCD array. The assembly may optionally include a support means for supporting one or more objects to be imaged. A housing may also be included in which the imager and fish eye lens, and optionally the support means, are positioned.

Figure 1:
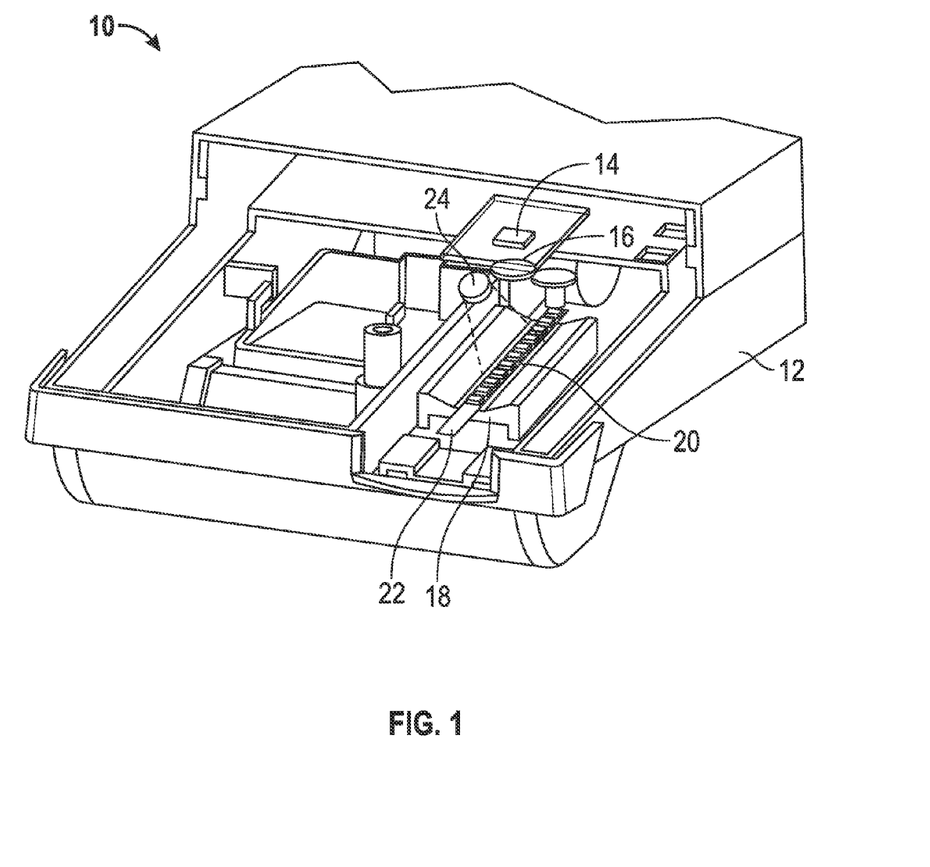
FIG. 1 shows a new and improved analyzer according to a version of the present disclosure.

Referring now to FIG. 1, shown therein is one embodiment of an imaging apparatus 10. The imaging apparatus 10 is provided with a housing 12, a detector 14, a wide-angle lens 16 operatively coupled to the detector 14, and a support 18. The detector 14 is positioned within the housing 12 and may be positioned above one or more target area 20 to be imaged. The detector 14 has a field of view encompassing the target area 20. The wide-angle lens 16 may be coupled to the detector 14 such that the detector 14 receives image data indicative of the target area 20 through the wide-angle lens 16.

The detector 14, which may also be referred to as an imager 14, may be a camera, CCD, CMOS, or any other suitable image capture device or device configured to detect optical signals or light and to convert optical signals into electrical signals, such as a small-format CCD/CMOS imager or a 2D CCD array as described above, for example. It is to be understood that various aperture sizes or detection areas may be used with the detector 14. The detector 14 may be configured to detect an optical signal or light reflected from one or more area of interest on one or more test component 22 and emitted by a light source. The detector 14 is not limited to an optical imager in the visible spectrum of light, but may include a microwave imaging system, an X-ray imaging system, and other desired imaging systems. Non-exclusive examples of the detector 14 may include optical imaging systems, spectrophotometers, microscopes, infrared sensors, and combinations thereof, for example. The detector 14 may be further configured to generate an electrical signal indicative of the strength or intensity (or other qualities, properties, or attributes) of the detected signal or light. For example, in some embodiments, the detector 14 may generate electrical current which is proportional to the intensity or strength of an optical signal or light detected by the detector 14. The detector 14 may be connected to an interior surface of the housing 12, which may be implemented as a suitable support structure. In some embodiments, the detector 14 may be connected to other components of the imaging apparatus 10 to support and position the detector 14 such that the detector is positioned to obtain an image of the target area 20. In the embodiment shown in FIGS. 1, 1A, and 1B, the detector 14 may be positioned such that the support 18 and the one or more test component 22 may slide under the detector 14 and be positioned such that the one or more test component 22 is within the one or more target area 20.

The housing 12 may, in one embodiment, have a travel surface for the support 18 to move into and out of the housing 12 such that the one or more test component 22 may be positioned on the support 18 and placed within the housing at the target area 20. The housing 12 may be formed from plastic, composite, metal, or any other suitable material.

The wide-angle lens 16, which may be called a fish eye lens, may have a field of view between about 110° to about 220°, for example. In one embodiment, the wide-angle lens 16 has a field of view of about 140°. The wide-angle lens 16 may be connected to the housing 12 to provide support for the wide-angle lens 16 and position the wide-angle lens 16 between the detector 14 and the one or more target area 20 to be imaged. In one embodiment, the wide-angle lens 16 is positioned between the detector 14 and the one or more target area 20 such that the combination of detector 14 and wide-angle lens 16 may be calibrated to focus the image received by the detector 14 on the one or more target area 20. The wide-angle lens 16 may be formed from glass, plastic, or any other suitable material to enable the detector 14 to receive the image of the one or more target area 20 through the wide-angle lens 16.

Figure 1A:
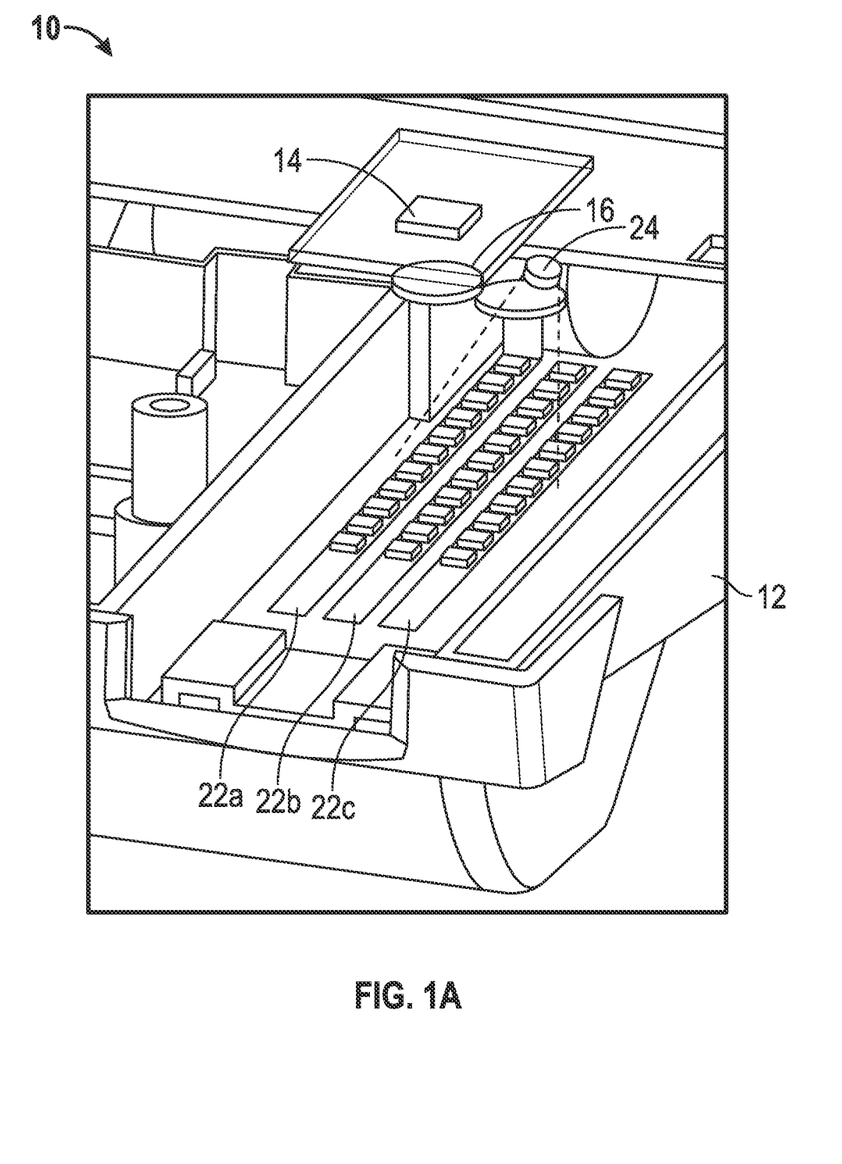
FIG. 1A shows another example of the analyzer of FIG. 1, receiving a plurality of test strips in accordance with the present disclosure.
Figure 1B:
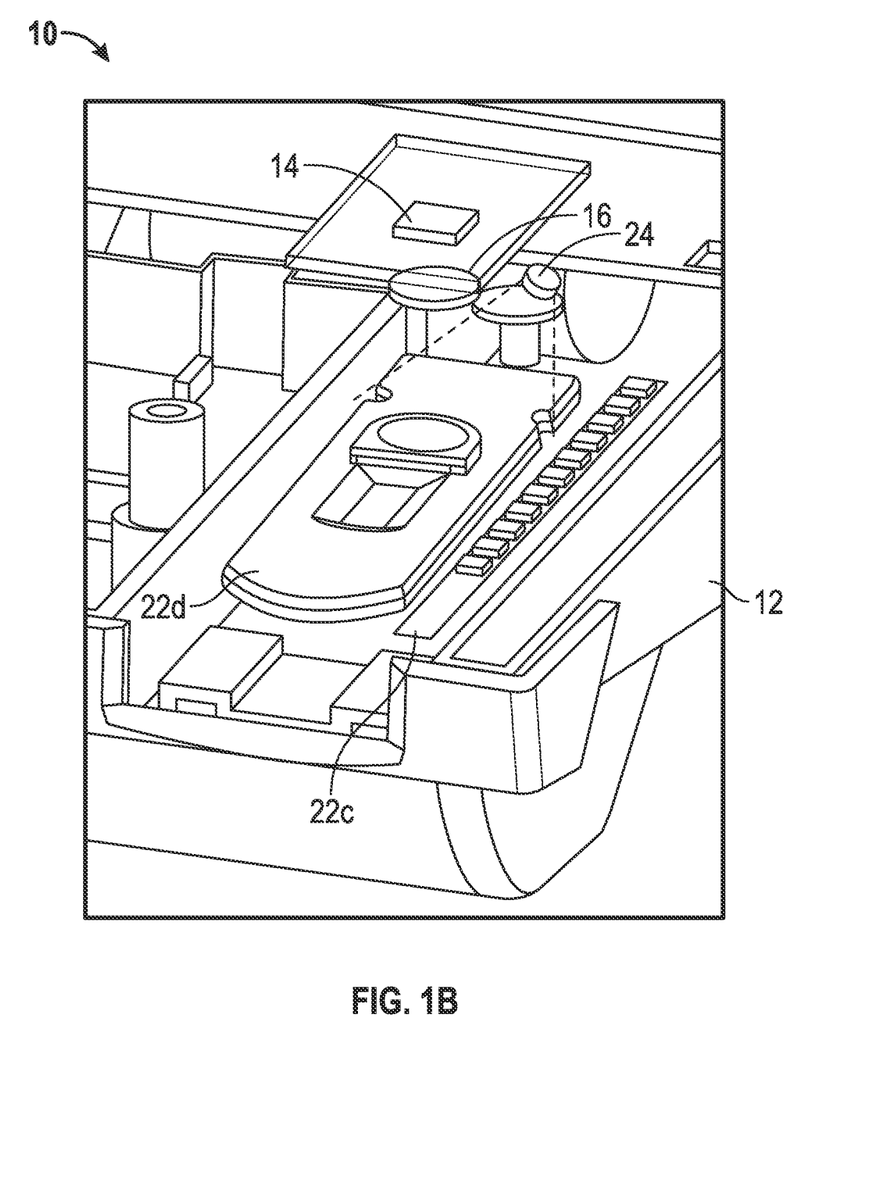
FIG. 1B shows one embodiment of the analyzer of FIG. 1, configured to receive a plurality of differing test components, in accordance with the present disclosure.

The support 18 may be positioned within the target area 20 and may be configured to receive one or more test component 22. The support 18 may be formed from plastic, metal, or any other suitable material. The test component 22 may be any diagnostic test component that can be optically read, such as lateral flow tests, reagent cards, reagent cartridges, microfluidic chips, reagent strips, and the like. Where the support 18 is configured to receive a plurality of test components 22, the test components 22 may be the same or similar test components or may differ in type. For example, as shown in FIG. 1A, the support (not shown) may be configured to receive the plurality of test components 22a-22c with the plurality of test components 22a-22c being all of the same type, such as the reagent strips depicted. In another embodiment, as shown in FIG. 1B, the support (not shown) may be configured to receive the plurality of test components 22d and 22c with the plurality of test components 22d and 22c being of differing types, such as the test component 22c being a reagent strip and the test component 22d being a reagent cartridge, for example.

In one embodiment, the imaging apparatus 10 may be provided with a light source 24 to illuminate the one or more test component 22 to enable the detector 14 to receive an image of the one or more test component 22. In one embodiment, the light source 24 may be located proximate to the detector 14 and connected to the housing 12. In other embodiments, the light source 24 may be positioned to illuminate the one or more test component 22 and positioned a distance from the detector 14. For example, the light source 24 may be positioned at a 45° angle relative to the one or more test component 22 and a distance from the detector 14 such that reflections of light from the one or more test component 22 are received by the detector 14. In addition, positioning the light source a distance away from the detector 14 prevents the detector 14 from blocking the light illuminating the one or more test component 22, as shown in FIGS. 1 and 1B. In this embodiment, the 45° angle may enable the detector 14 to be used in a manner similar to a reflectometer. The light source 24 may include any suitable device such as a light emitting diode, a laser, or a quantum-well emitter, an incandescent bulb or tube, a fluorescent light bulb or tube, a halogen light bulb or tube, or any other desired light source or object configured to emit an optical signal having any desired intensity, wavelength, frequency, or direction of propagation, for example. The light source 24 may have any wavelength, including an adjustable wavelength, a substantially constant wavelength(s), and combinations thereof, for example. In one embodiment, the wavelength(s) are within the visible spectrum. The light source 24 may emit any desired optical beam, having an angular spread varying between about 0° to about 5°, or more, for example. In some exemplary embodiments, the light source 24 may be implemented, as a first and a second light sources 24, and such first and second light sources 24 may have different locations and/or orientations so that the first and second light sources 24 may cooperate to illuminate substantially the entire field of view of the detector 14. The light source 24 may be attached to the housing 12 in any suitable manner, such as by adhesives, welds, bolts, seams, joints, and combinations thereof, for example. In some exemplary embodiments, the light source 24 and the housing 12 may be implemented as a unitary body, while in some exemplary embodiments the housing 12 may be omitted and the light source 24 may be directly attached to the support 18, or to any other desired component of the imaging apparatus 10. The light source 24 may be powered with any suitable power source and/or control source configured to power the light source 24 and control the strength and intensity of the light emitted by the light source 24, for example. As will be readily appreciated by one skilled in the art having the benefit of the instant disclosure, it may be desirable that the light source 24 emits a light having a relatively or substantially constant strength or intensity, although such strength or intensity may be adjustable to calibrate the imaging apparatus 10 and the detector 14, for example. To that end, a controller (not shown) may be operably coupled with the light source 24 and may be configured to ensure that the light source 24 emits a substantially constant light and/or to calibrate the light source 24.

As will be appreciated by persons of ordinary skill in the art having the benefit of the instant disclosure, the light emitted by the light source 24 may be processed, conditioned, filtered, diffused, polarized, or otherwise conditioned by one or more lenses (not shown), filters (not shown), collimators (not shown), diffusers (not shown), refractors (not shown), prisms (not shown), and other devices, or combinations thereof, prior to being detected by the detector 14, for example.

Further, in some embodiments of the inventive concepts disclosed herein, the light source 24 may be supported above the target area 20 in any desired manner, such as by being connected to the housing 12 (e.g., via joints, seams, bolts, brackets, fasteners, welds, or combinations thereof), or by the support 18, or by any other desired component of the imaging apparatus 10.

As will be appreciated by persons skilled in the art, in some embodiments of the inventive concepts disclosed herein, more than one light source 24 may be implemented, such as two or more than two light sources 24.

Figure 2:
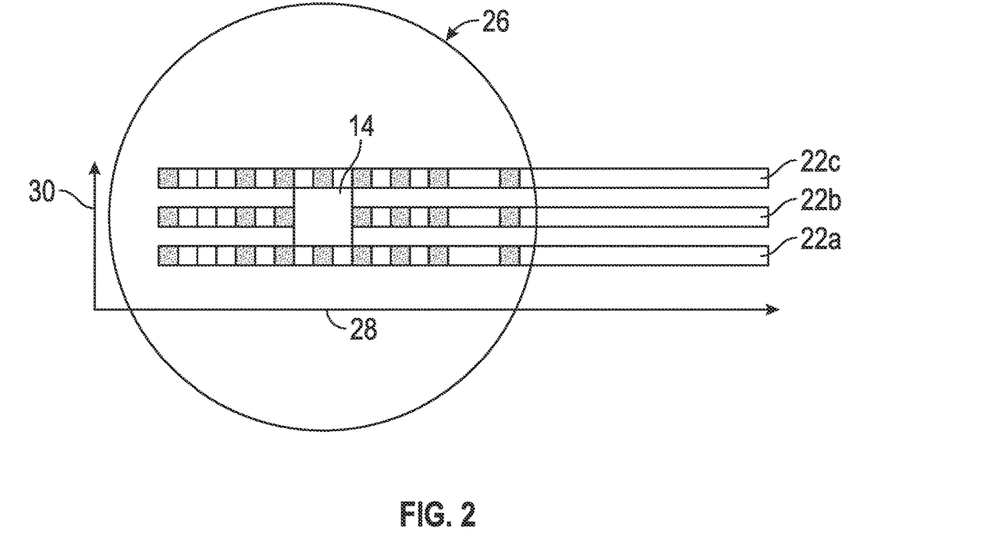
FIG. 2 shows an embodiment of an imaging device with a fish eye lens positioned relative to multiple reagent strips in accordance with the present disclosure.
Figure 3:
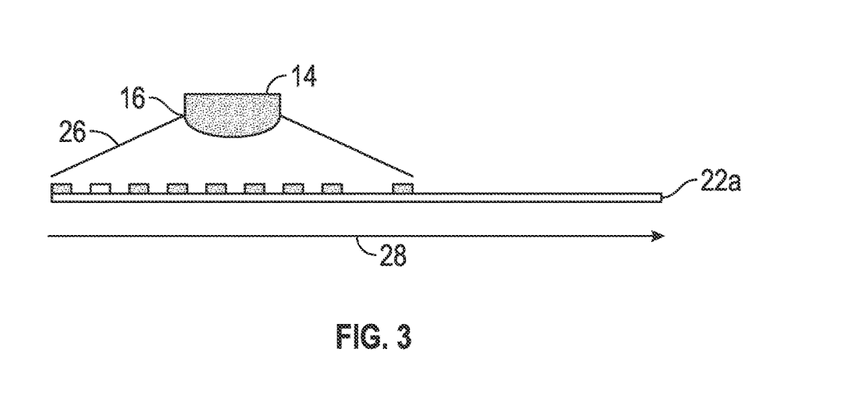
FIG. 3 shows a side view of the arrangement of the imaging device of FIG. 2.

Referring to FIGS. 2 and 3, in one embodiment, the imager 14, also referred to herein as the detector 14, and fish eye lens 16, also referred to herein as the wide-angle lens 16, are arranged such that the fish eye lens 16 is positioned a predetermined distance from the target area 20 or object to be imaged, such as the one or more test component 22. The predetermined distance is less than the distance that would be optimal or necessary to image the same field of view with a regular lens. Furthermore, the imaging apparatus 10 allows for the placement of the imager 14 directly above the target area 20 to be imaged in smaller desktop apparatuses that have low profiles. FIG. 2 shows the detector 14, in this embodiment a CCD array, and the fish eye lens 16 above three strips 22a-c and having an approximate field of view 26. It is understood that reagent strips are used as an example of the one or more test component 22, but the detector 14 and the fish eye lens 16 could be used with any diagnostic test component that can be read optically. Where an imaging apparatus is not provided with the wide-angle lens 16, the detector 14, such as a CCD array, would only be able to view with a conventional lens either a small area down the center line of the strip or other test component 22, approx 1.5 mm wide, when using a linear 1D CCD array or if using a 2D array the same field of view but with the lens and CCD array mounted a long way from the strip or other test component 22. When using the detector 14, such as a 2D array, and the wide-angle lens 16, such as a fish eye lens, the optics can be more compact, while still allowing a wide viewing angle in two dimensions, allowing the array to see the whole test component 22, such as a test strip, length wise, along a first axis 28, but also to allow additional test components 22, such as additional strips, for example, to be viewed on a second axis 30.

Conventionally, using test strips as test components 22, the strip is measured length ways, along the first axis 28, with multiple measurements to be made along the center line of the strip, with the 2D array multiple samples can also not be made across the pad compensating for the possible lack of resolution along the pad at the extremes of the field of view.

Referring to FIG. 3 which shows, a side view of the detector 14, which may be a CCD array, the wide-angle lens 16, and test component 22, which may be a strip. The field of view 26 is marked at approximately 140°, but this may be wider if needed as previously described, depending on the particular type of wide-angle lens 16 used. Of note is that the wide-angle lens 16 may be mounted very close to the test component 22, such as the strip, thereby reducing the size of the optics system and the imaging apparatus 10, but also allowing the flexibility to measure multiple test components 22, whether strips, slides, or a combination thereof, extending the flexibility for future test type development.

In another aspect, the invention is embodied as an improvement to traditional optical analyzers, such as reflectometers. Examples of such analyzers are the CLINITEK STATUS® and CLINITEK ADVANTUS® urine chemistry analyzers sold by Siemens Healthcare Diagnostics (Tarrytown, N.Y.). The present disclosure can improve on traditional analyzers by reducing the distance the imager needs to be from the object to be imaged while still retaining the necessary field of view. The result is a more compact imaging apparatus. This leads to a smaller instrument which is very desirable. In one embodiment, the optical analyzer includes the imager 14 and the fish eye lens 16, as described above. In addition, the analyzer may include the support 18 for supporting one or more objects to be imaged. The support 18 may be a platform, a tray, clips or any other suitable mechanism for supporting an object to be imaged. It is understood that the means would vary depending on the shape and number of the objects to be imaged. If the object to be imaged is one or more urine strips, the support 18 supports the strips in a manner that they can be imaged by the imager 14.

The methods and systems described herein are not limited to a particular hardware or software configuration, and may find applicability in many computing or processing environments. The methods and systems may be implemented in hardware or software, or a combination of hardware and software. The methods and systems may be implemented in one or more computer programs, where a computer program may be understood to include one or more processor executable instructions.

Figure 4:
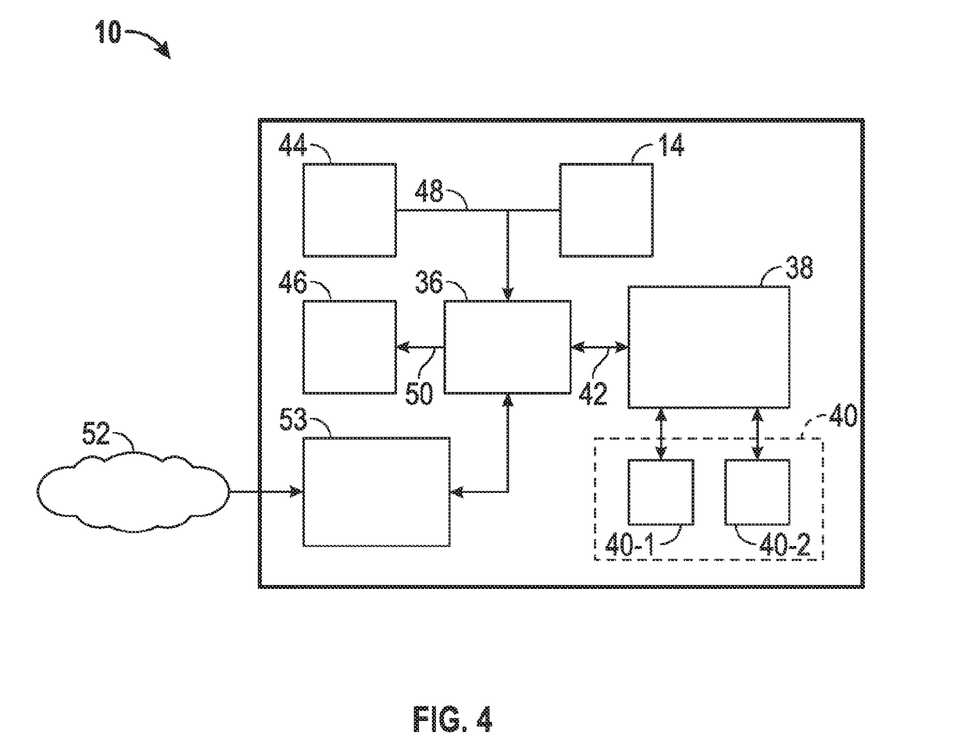
FIG. 4 shows a block diagram of an embodiment of an imaging apparatus with a processor and processor-readable memory in accordance with the present disclosure.

Referring now to FIG. 4, in one embodiment, the imaging apparatus 10 may be provided with a processor 36, a processor-readable memory 38, and have processor executable instructions 40 stored on the processor-readable memory 38 to capture the images and analyze the images as discussed herein. The processor 36 may be implemented as a single processor or multiple processors working together or independently to execute the processor executable instructions 40 described below. Embodiments of the processor 36 may include a digital signal processor (DSP), a central processing unit (CPU), a microprocessor, a multi-core processor, an application specific integrated circuit, and combinations thereof. The processor 36 is coupled to the processor-readable memory 38. The non-transitory processor-readable medium 38 may be implemented as RAM, ROM, flash memory, or the like, as described in more detail below. The processor-readable memory 38 may be a single non-transitory processor-readable memory, or multiple non-transitory processor-readable memories functioning logically together or independently.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation. For example, as shown in FIG. 4, the processor 36 is coupled to and configured to communicate with the processor-readable memory 38 via a path 42 which can be implemented as a data bus, for example. The processor 36 may be capable of communicating with an input device 44 and an output device 46 via paths 48 and 50, respectively. Paths 48 and 50 may be implemented similarly to, or differently from path 42. For example, paths 48 and 50 may have a similar or different number of wires and may or may not include a multidrop topology, a daisy chain topology, or one or more switched hubs. The paths 42, 48, and 50 can be a serial topology, a parallel topology, a proprietary topology, or combinations thereof. The processor 36 is further capable of creating, manipulating, altering, and storing data objects and computer data structures into the processor-readable memory 38

References to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application and where such memory may be non-transitory in nature. For example, as shown in FIG. 4, the processor-readable memory 38 stores the processor executable instructions 40 and may be implemented, as described above, as RAM, a hard drive, a hard drive array, a solid state drive, a flash drive, a memory card, or the like, as well as combinations thereof. When more than one processor-readable memory 38 is used, one of the processor-readable memories 38 may be located in the same physical location as the processor 36, and another one of the non-transitory processor-readable memories 38 may be located in a location remote from the processor 36. The physical location of the processor-readable memories 38 may be varied and the processor-readable memories 38 may be implemented as a "cloud memory," i.e. processor-readable memory 38 which is partially or completely based on or accessed using a network 52 which may be accessed by the processor 36 using a communications device 53

The processor executable instructions 40, also referred to herein as computer program(s), may execute on one or more programmable processors 36, and may be stored on one or more storage medium readable by the processor (including volatile and non-volatile memory and/or storage elements), the processor-readable memory 38, one or more input devices 44, and/or one or more output devices 46. The processor 36 thus may access one or more input devices 44 to obtain input data, and may access one or more output devices 46 to communicate output data. The input and/or output devices 44 and 46 may include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation. The input device 44 transmits data to the processor 36, and may additionally be implemented as the detector 14, a keyboard, a touch-screen, a camera, a track ball, a microphone, a network adapter, and combinations thereof. The input device 44 may be located in the same location as the processor 36 and communicate with the processor 36 via path 48. The output device 46 may transmit information from the processor 36 to a user, such that the information can be perceived by the user. For example, the output device 46 may additionally be implemented as a touch-screen, an LCD screen, a printer, or any other suitable output device. The output device 44 communicates with the processor 36 via the path 50.

References herein to microprocessor instructions, microprocessor-executable instructions, processor executable instructions, or computer program(s), in accordance with the above, may be understood to include programmable hardware. The computer program(s) 40 may be implemented using one or more high level procedural or object-oriented programming languages to communicate with a computer system; however, the program(s) 40 may be implemented in assembly or machine language, if desired. The language may be compiled or interpreted.

As provided herein, in one embodiment, the processor(s) 36 may thus be embedded in one or more devices that may be operated independently or together in a networked environment. For example, although described in FIG. 4 as being integral to the imaging apparatus 10, the processor 36, the non-transitory processor-readable memory 38, and the processor executable instructions 40 may be implemented separate from the imaging apparatus 10, as a mobile device, mobile computer system, laptop, tablet, or computer system, for example. The computer system may have a connection to the imaging apparatus 10 capable of and configured to transmit image data captured by the detector 14 to the processor 36 and the processor-readable memory 38. The connection between the computer system and the imaging apparatus 10 may also enable the processor 36 to transmit instructions from the processor executable instructions 40 stored on the processor-readable memory 38 to the imaging apparatus 10. The device(s) or computer systems that integrate with the processor(s) 36 may also include, for example, a personal computer(s), workstation(s) (e.g., Sun, HP), personal digital assistant(s) (PDA(s)), handheld device(s) such as cellular telephone(s) or smart cellphone(s), laptop(s), handheld computer(s), or another device(s) capable of being integrated with a processor(s) that may operate as provided herein. Accordingly, the devices provided herein are not exhaustive and are provided for illustration and not limitation.

References to a network, unless provided otherwise, may include one or more intranets and/or the internet. The network 52 may permit bi-directional communication of information and/or data between the processor 36, the network 52, and the detector 14. The network 52 may include, for example, a Local Area Network (LAN), wide area network (WAN), and/or may include an intranet and/or the internet and/or another network. The network(s) 52 may be wired or wireless or a combination thereof and may use one or more communications protocols and a plurality of network topographies to facilitate communications between the different processors 36, such as Ethernet, TCP/IP, circuit switched paths, file transfer protocol, packet switched wide area networks, and combinations thereof. Additionally, the network 52 may interface with the processor 36 in a variety of ways, such as by optical and/or electrical interfaces. The processors 36 may be configured for distributed processing and may utilize, in some embodiments, a client-server model as needed. Accordingly, the methods and systems may utilize multiple processors and/or processor devices, and the processor instructions may be divided amongst such single- or multiple-processor/devices.

Figure 5A:
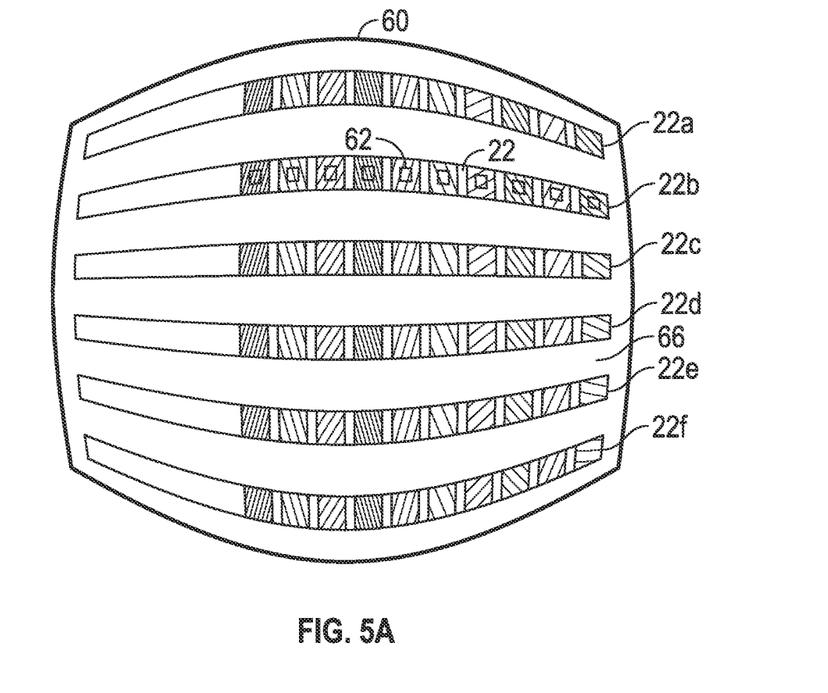
FIGS. 5A and 5B show an example of an image captured with the imaging device and converted into a rectilinear image by an embodiment of the devices and methods of the present disclosure.
Figure 5B:
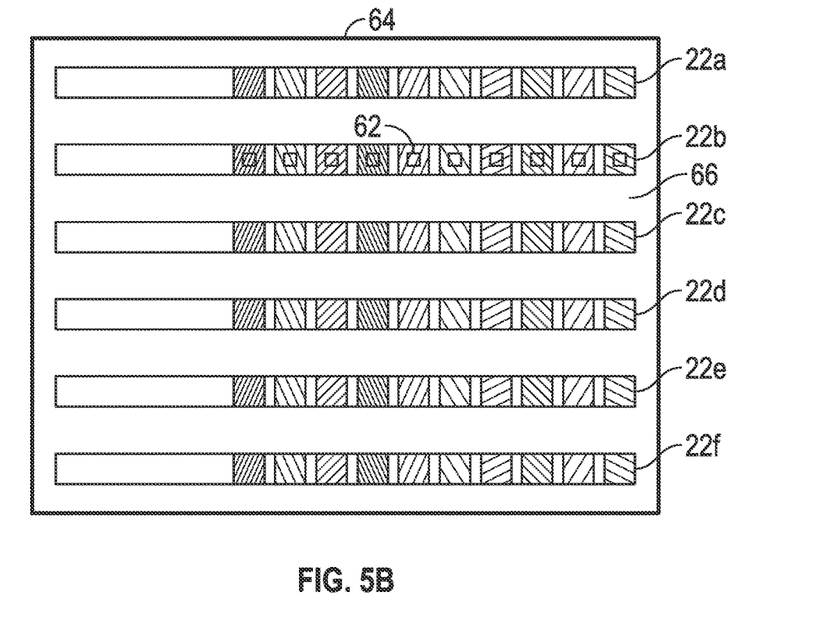

In one embodiment, in use, the processor executable instructions 40 may cause the detector 14 to capture an image 60 of the one or more test component 22 proximate to the target area 20 through the fish-eye lens 16. The fish-eye lens 16 causes the image 60 to have a warped appearance in which the test components 22 are captured with an arc-shape rather than a linear shape. An embodiment of the image 60 is shown in FIG. 5A. The image 60 may be transmitted by the detector 14 to the processor 36 as an optical signal, an electrical signal, and/or combinations thereof. In one embodiment, the image 60 may have a matrix of pixels, with each pixel having red, green, and blue (RGB) values indicative of its reflectance value. In an exemplary embodiment, the image 60 may have two or more predetermined regions of pixels, each predetermined region of pixels corresponding to a read position of the one or more test component 22 supported by the support 18 in the field of view of the detector 14. The processor executable instructions 40 may then cause the processor 36 to identify a type of the one or more test component 22 and one or more area of interest 62 within each of the one or more test component 22 in the image 60, as shown in FIGS. 5A and 5B. The processor 36 may then analyze the one or more area of interest 62 within the image 60 to determine a presence of and/or content of an analyte of interest within a sample applied to the one or more test component 22 at the one or more area of interest 62. In the example shown in FIG. 5A, six separate test components 22*a-f* are depicted. In this example, each of the test components 22*a-f* have 10 reagent pads which are referred to herein as areas of interest 62 in the image 60.

During analysis of the one or more area of interest 62, in some embodiments, the processor 36 may then read RGB values 76 for pixels indicative of the one or more areas of interest 62 within the image 60 to calculate the presence and/or content of the analyte of interest of the sample applied to the reagent pads depicted within the one or more areas of interest 62. Each optical or other signal indicative of the reflectance value of the one or more area of interest 62 may have a different magnitude relating to a different wavelength of light (i.e. color). The color of the one or more area of interest 62 may be determined based on the relative magnitudes of the reflectance signals of various color components, for example the RGB values. Additionally, during analysis of the one or more area of interest 62, the processor 36 may control and adjust for variables affecting the image 60 such as variations in light provided by light source 24 across the one or more test component 22 and adjust a calibration of the detector 14 based on the variations in light across the one or more test components 22.

As shown in FIG. 5A, the image 60 captured by the detector 14 displays six test components 22. The image 60 may be non-rectilinear due to the detector 14 receiving the image data through the wide-angle lens 16. In some embodiments, the image 60 is converted to a rectilinear image 64, shown in FIG. 5B, prior to the processor analyzing the one or more area of interest 62. The conversion to the rectilinear image 64 may be performed, in some embodiments, by determining pixel values for the one or more areas of interest 62, the one or more test component 22, and a background 66 and applying the pixel values to a template to create the rectilinear image 64. In other embodiments, the pixel values may be mapped and converted to the rectilinear image 64 by determining a size and location of the one or more test component 22 and the one or more areas of interest 62 depicted within the image 60 to organize coordinates and pixel values and to stretch the shape of the image 60 to form the rectilinear image 64.

Figure 6:
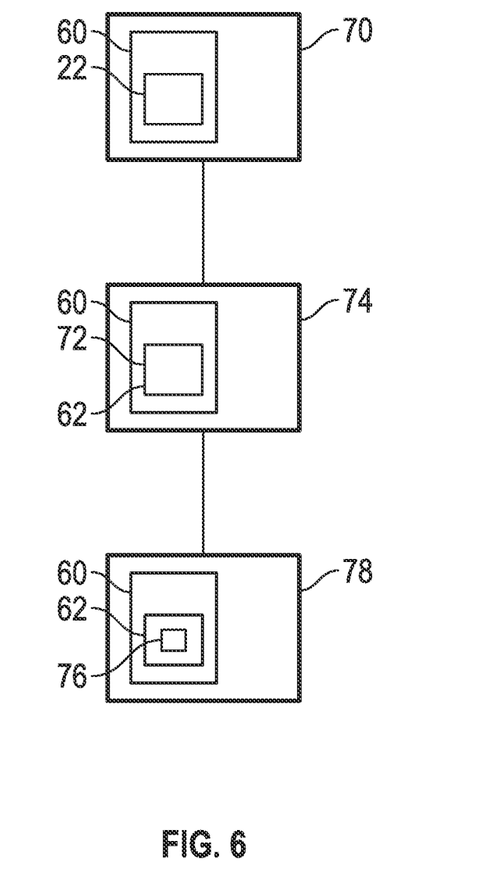
FIG. 6 shows a block diagram of a processor executable method of using an imaging device in accordance with the present disclosure.

Referring now to FIG. 6, therein shown is one embodiment of processor executable instructions 40 employing a method for using the imaging apparatus 10. The processor executable instructions 40 may cause the detector 14 to capture the image 60 of one or more test component 22. The processor 36 may then identify the one or more test component 22 within the image 60 and determine a type of the one or more test component 22, as indicated by block 70. The processor 36 may then determine a location 72 of each of the one or more areas of interest 62 within the image and map the location 72 of each of the one or more areas of interest 62 based on the type of the one or more test component 22, as indicated by block 74. The processor 36 may then read RGB values 76 for pixels indicative of the one or more areas of interest 62 within the image 60 to determine a presence of an analyte of interest within a sample applied to the one or more test components 22, as indicated by block 78. In one embodiment, the processor 36 may also perform a rectilinear transformation of the image 60 formed by the detector 14 using the wide-angle lens 16, as described above, to form the rectilinear image 64, as shown in FIGS. 5A and 5B, prior to determining the one or more region of interest 76.

In another embodiment where a single test component is to be imaged, the processor executable instructions 40, when executed by the processor 36, may cause the detector 14 to capture the image 60 of the test component 22 on whatever surface it is placed, and identify the location of the test component 22 location on the surface on which it is placed. This may include the elimination of other items that may be on the same surface and which may confuse the processor executable instructions 40. Once the test component 22 is located, the processor 36 may determine the individual location of one or more test pad on the test component 22. This may include differentiating a number of pads for all of the types of test components 22 in use. Once the number of pads and the location of each pad on the test component 22 has been identified, the processor 36 may determine the region of interest 62 in each pad. Once the region of interest 62 on each pad has been determined, the processor 36 may take RGB values for the pixels indicative of the region of interest 62 for each of the pads to use in algorithms that calculate the presence or absence of an analyte of interest within a sample applied to the pads.

The processor 36 may control and adjust for variables affecting the image 60 such as variations in light across the one or more test component 22. The processor 36 may also control and adjust for calibration of a camera system, such as the detector 14. Where the processor 36 may interact with multiple imaging apparatuses, the processor 36 may adjust for calibration from camera to camera. If multiple samples are required to determine the result, kinetic measurement, the processor 36 may control and adjust for light source variations across the pads and variations from measurement to measurement.

The image 60 and other subsequent images received by the detector 14 or processed by the processor 36 may be raw images, jpeg, bitmaps, or any other suitable image files. The raw images and or the converted images may be stored in memory or a database and may be transmitted over a network for analysis or storage.

In a further aspect, the invention is embodied as a method of manufacturing the assembly described above. The manufacturing method would include coupling the wide-angle lens 16 to the detector 14 such that the detector 14 receives image data of the target area 20 through the wide-angle lens 16. The wide-angle lens 16 may be positioned a predetermined distance from the target object to be imaged. The method is further performed by coupling a computer system to the detector 14, the computer system having the processor 36 and the processor-readable memory 38 storing processor executable instructions 40 discussed in detail above.

The test components 22 may be urine strips (hereinafter "strips"). The method includes imaging strips utilizing the imager 10, the detector 14, operatively coupled to the fish eye lens 16 to reduce the distance the detector 14 needs to be from the strips in order to image them. It is understood that the strips may be any diagnostic test that can be optically read, such as lateral flow tests, reagent cards, reagent cartridges, microfluidic chips, and the like.

In one example, software code can be stored on the phone or analyzer and have a processor carry out the following steps.

The steps to convert the image 60 shown in FIG. 5A to the rectilinear image 64 shown in FIG. 5B that can be used by the instrument to measure urinalysis results include:

I. Take the initial picture of the strip on what ever surface it is placed.

II. Identify the strip location on the surface placed. This may include the elimination of other items that potentially could be on the same surface confusing the software.

III. Once the strip is located, isolate the individual location of each pad on the strip. This would include being able to differentiate the number of pads for all of the types of strips that are available to be used with the analyzer.

IV. Once the number of pads and the location of each pad has been identified, the strip type is determined so that the software knows which pad was in which location.

V. Now that the pad locations and type are known, the software would workout the region of interest in each pad.

VI. Once the region of interest on each pad is found, RGB values in the image are extracted for these pads to use in algorithms that calculate content of any reagent.

VII. Control and adjust for the following variables: variations in light source across the strip; calibration of the camera system—camera to camera; if multiple samples are required to determine the result—kinetic measurement, we have the light source variations across the pads and variations from measure to measure. The raw images and or the converted images may be stored in memory or a database and may be transmitted over a network for analysis or storage.

While the present invention has been described in connection with the exemplary embodiments of the various figures, it is not limited thereto and it is to be understood that other similar embodiments may be used or modifications and additions may be made to the described embodiments for performing the same function of the present invention without deviating therefrom. Therefore, the present invention should not be limited to any single embodiment, but rather should be construed in breadth and scope in accordance with the appended claims. Also, the appended claims should be construed to include other variants and embodiments of the invention, which may be made by those skilled in the art without departing from the true spirit and scope of the present invention.

What is claimed is:

1. An imaging apparatus, comprising:
   a housing;
   a detector positioned within the housing and having a field of view encompassing one or more target area within the housing to be imaged;
   a wide-angle lens operatively coupled to the detector such that the detector receives image data of the target area through the wide-angle lens; and
   a support positioned at the target area and configured to receive one or more test component,
   wherein the one or more test component is a plurality of test components and the detector is configured to image the plurality of test components simultaneously,
   wherein the wide-angle lens has a field of view between about 110° to 220°.

2. The imaging apparatus of claim 1, wherein the detector is a CCD array.

3. The imaging apparatus of claim 2, wherein the CCD array is a 2D CCD array.

4. The imaging apparatus of claim 1, wherein the wide-angle lens is a fish eye lens.

5. The imaging apparatus of claim 1, wherein the detector is positioned directly above the target area to be imaged.

6. An imaging apparatus, comprising:
   a housing;
   a detector positioned within the housing and having a field of view encompassing one or more target area within the housing to be imaged;
   a wide-angle lens operatively coupled to the detector such that the detector receives image data of the target area through the wide-angle lens;
   a support positioned at the target area configured to receive one or more test component; and
   a computer system having a processor configured to:
      receive an image captured by the detector and analyze one or more area of interest within the image to determine at least one of a presence and an absence of an analyte within a sample applied to the one or more test component at the one or more area of interest,
   wherein the computer system is further configured to enable the detector to capture an image of one or more test component at the target area,
   wherein analyzing the one or more area of interest further comprises taking RGB values for the one or more area of interest and controlling and adjusting for variations in light across the one or more test component.

7. The imaging apparatus of claim 6, wherein the detector is a CCD array.

8. The imaging apparatus of claim 7, wherein the CCD array is a 2D CCD array.

9. The imaging apparatus of claim 6, wherein the wide-angle lens is a fish eye lens.

10. The imaging apparatus of claim 9, wherein the wide-angle lens has a field of view between about 110° to 220°.

11. The imaging apparatus of claim 6, wherein the one or more test component is a plurality of test components and the detector is configured to image the plurality of test components simultaneously.

12. The imaging apparatus of claim 6, wherein capturing an image of the one or more test component further comprises calibrating the detector.

13. The imaging apparatus of claim 6, wherein the computer system is further configured to identify one or more area of interest within each of the one or more test component in the image.

14. A method, comprising:
   coupling a wide-angle lens to a detector such that the detector receives image data of a target area through the wide-angle lens; and
   coupling a computer system to the detector, the computer system having a processor and one or more processor-readable memory storing processor executable instructions that when executed cause the processor to:

enable the detector to capture an image of one or more test component proximate to the target area;

identify one or more area of interest within each of the one or more test component in the image; and analyze the one or more area of interest within the image to determine at least one of a presence and an absence of an analyte within a sample depicted within the one or more area of interest, wherein analyzing the one or more area of interest further comprises taking RGB values for the one or more area of interest and controlling and adjusting for variations in light across the one or more test component.

15. The method of claim 14, further comprising operably coupling a light source to the computer system to illuminate the target area.

\* \* \* \* \*